(12) United States Patent
Lund-Clausen et al.

(10) Patent No.: US 9,427,244 B2
(45) Date of Patent: Aug. 30, 2016

(54) OBJECT CAPTURE DEVICE

(71) Applicant: Cook Medical Technologies LLC, Bloomington, IN (US)

(72) Inventors: Jacob Lund-Clausen, Kgs. Lyngby (DK); Palle Munk Hansen, Bjaerverskov (DK); Petar Mihaljevic, St. Fugelede (DK); Kerstin Svensson, Koege (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 270 days.

(21) Appl. No.: 14/371,323

(22) PCT Filed: Dec. 7, 2012

(86) PCT No.: PCT/US2012/068482
§ 371 (c)(1),
(2) Date: Jul. 9, 2014

(87) PCT Pub. No.: WO2013/106146
PCT Pub. Date: Jul. 18, 2013

(65) Prior Publication Data
US 2015/0005781 A1    Jan. 1, 2015

(30) Foreign Application Priority Data

Jan. 10, 2012  (GB) .................................. 1200333.1

(51) Int. Cl.
*A61B 17/221*     (2006.01)
*A61B 17/00*      (2006.01)
(52) U.S. Cl.
CPC .... *A61B 17/221* (2013.01); *A61B 2017/00867* (2013.01); *A61B 2017/2215* (2013.01)
(58) Field of Classification Search
CPC .......... A61B 17/221; A61B 17/32056; A61B 2017/2212–2017/2217; A61F 2/01; A61F 2/013; A61F 2002/011; A61F 2002/015–2002/018
See application file for complete search history.

(56) References Cited

U.S. PATENT DOCUMENTS

| | | | | |
|---|---|---|---|---|
| 4,243,040 A | * | 1/1981 | Beecher | A61B 17/22032 604/271 |
| 4,324,262 A | * | 4/1982 | Hall | A61B 10/02 600/569 |
| 4,946,440 A | * | 8/1990 | Hall | A61B 18/08 600/569 |

(Continued)

OTHER PUBLICATIONS

European Patent Office, International Search Report of International Application No. PCT/US2012/068482, Mailed on Mar. 12, 2013, 3 pages.

*Primary Examiner* — Julian W Woo
*Assistant Examiner* — Shaun L David
(74) *Attorney, Agent, or Firm* — Brinks Gilson & Lione

(57) ABSTRACT

A medical device for collecting objects from a body lumen comprises a catheter, a basket having a closed first end and an open second end, and an actuator connected to the closed first end of the basket, the catheter and basket moveable relative to one another between a first configuration and a second configuration to draw objects from a body lumen into the basket. In the first configuration the closed first end of the basket is inside the catheter and the open second end is everted over at least a part of the closed first end. The apparatus may be actuated to pull the closed first end of the basket further into the catheter and invert the second end of the basket, the second end scraping the sides of the lumen as it inverts, surrounding an object in the lumen, and drawing the object into the basket.

20 Claims, 2 Drawing Sheets

(56) References Cited

U.S. PATENT DOCUMENTS

| | | | |
|---|---|---|---|
| 5,171,305 A * | 12/1992 | Schickling | A61M 25/0119 604/271 |
| 7,621,870 B2 | 11/2009 | Berrada et al. | |
| 7,780,696 B2 | 8/2010 | Daniel et al. | |
| 2003/0176884 A1 * | 9/2003 | Berrada | A61F 2/013 606/200 |
| 2007/0038227 A1 * | 2/2007 | Massicotte | A61B 17/22032 606/127 |
| 2007/0112374 A1 * | 5/2007 | Paul | A61F 2/013 606/200 |
| 2007/0149996 A1 | 6/2007 | Coughlin | |
| 2007/0213765 A1 | 9/2007 | Adams et al. | |
| 2009/0299393 A1 * | 12/2009 | Martin | A61B 17/221 606/159 |
| 2010/0030256 A1 | 2/2010 | Dubrul et al. | |
| 2010/0137846 A1 | 6/2010 | Desai et al. | |
| 2010/0249815 A1 | 9/2010 | Jantzen et al. | |
| 2011/0288572 A1 * | 11/2011 | Martin | A61B 17/221 606/159 |

\* cited by examiner

OBJECT CAPTURE DEVICE

CROSS-REFERENCE TO RELATED APPLICATIONS

This application is a 371 national stage application of PCT Application No. PCT/US2012/068482, filed Dec. 7, 2012, which application claims the benefit of GB Application No. GB 1200333.1, filed on Jan. 10, 2012, entitled "OBJECT CAPTURE DEVICE," the entire contents of which are incorporated herein by reference.

TECHNICAL FIELD

The present invention relates to an object capture device as well as to a method of capturing objects from a body lumen, particularly for the capture of thrombi in a patient's vasculature.

BACKGROUND ART

It is known that material may form or build up in vessels of the circulatory system; such material may seriously compromise the health of the patient. For example, thrombi or blood clots may form and may partially or completely occlude a blood vessel, decreasing or even completely cutting off blood flow through the vessel. The thrombus may adhere to the vessel wall or may be dislodged, becoming free floating in the vessel. A free floating thrombus, also known as an embolus, may travel along a vessel and eventually cause a blockage in a distant part of the body, such as the heart or the brain, with potentially lethal consequences.

Various devices are known for capturing and removing thrombi and other objects from a patient's blood system. Such devices typically involve the use of a plurality of different tools which are deployed in different stages of the capture and removal procedure. For example, a first medical device may be introduced to break the thrombus into pieces so as to prevent it from blocking a vessel. However, breaking the thrombus into pieces can be harmful to the patient as dislodged parts may travel through the circulatory system and eventually block another vessel elsewhere. In order to avoid this, blocking and/or suction means are required to ensure that the dislodged parts are safely collected. For example, a filter may be positioned distal of the thrombus so as to catch the dislodged parts after the thrombus has been broken up by the first medical device. The material trapped by the filter can remain in place until removed using yet further apparatus such as an aspirator. Various prior art thrombus capturing devices are disclosed in US2010/0249815, U.S. Pat. No. 7,621,870, US 2007/0149996 and U.S. Pat. No. 7,780,696.

DISCLOSURE OF THE INVENTION

The present invention seeks to provide an improved object capture device and method, particularly for removing objects such as thrombi from a patient's vasculature.

The preferred embodiment provides a single tool for capturing and removing thrombi. This tool can be used in a single stage, thus facilitating the medical procedure quickly and easily. There is also disclosed a method for capturing and removing thrombi. In particular the invention provides a mechanism for pulling a thrombus away from a vessel wall. The device comprises an object collecting member, hereinafter referred to as a basket.

According to an aspect of the present invention there is provided a medical device for collecting objects from a body vessel, including: a catheter provided with a proximal end, a distal end and a lumen therethrough; an elongate basket provided with a closed first end and an open second end; and an actuator connected to the closed first end of the basket and extending through the lumen of the catheter to the proximal end of the catheter; wherein the catheter and the basket are movable relative to one another between a first configuration in which the first end of the basket is located within the distal end of the catheter and the second end of the basket extends radially out of the catheter and is everted over the first end of the basket, and a second configuration in which the first end of the basket is withdrawn into the catheter and the everted second end is at least partially inverted; and wherein, the medical device is operable so as to relatively move the catheter and the basket from said first configuration to said second configuration, said movement in use causing objects in a body vessel to be drawn into the basket.

The second end may be constrained in the first position and free from attachment or constraint in the second position.

The actuator may be, for example, a wire, rod or cable, hereinafter referred to as a wire.

In the second configuration at least part of the second end of the basket may be withdrawn into the catheter.

According to another aspect of the present invention there is provided a medical device for collecting objects from a body vessel, including: a catheter provided with a proximal end, a distal end and a lumen therethrough; an elongate basket provided with a first end and a second end; and an actuator connected to the first end of the basket and extending through the lumen of the catheter to the proximal end of the catheter; wherein the catheter and the basket are movable relative to one another between a first configuration in which the first end of the basket is located within the distal end of the catheter and the second end of the basket extends radially out of the catheter and is everted over the first end of the basket, the second end being constrained in position, and a second configuration in which the first end is withdrawn into the catheter and the everted second end is at least partially inverted, the second end being free from constraint; and wherein, the medical device is operable so as to release the second end from constraint, and move the catheter and the basket from said first configuration to said second configuration, said movement in use causing objects in a body vessel to be drawn into the basket.

The basket may be provided with a closed first end and an open second end. By providing a basket having a closed first end, the basket is able to pull, as if sucking, an object such as a thrombus into the basket.

Preferably the basket is made of spring steel, or shape memory material such as, for example, Nitinol, hereinafter referred to as shape memory material. Where the remembered shape is a generally tubular basket, on release of the second end of the basket the basket may spring radially outwardly and distally of the catheter to surround a thrombus. By providing a rolling basket which rolls outwardly during its deployment so as to position itself between a thrombus and the vessel wall in which the thrombus lies, the basket may surround the thrombus such that when the basket is withdrawn into the catheter the thrombus is withdrawn into the basket.

The everted portion of the basket may scrape against the vessel wall thus dragging any plaque or thrombus adhered thereto into the basket as the basket is reverted or inverted by withdrawal of the member into the catheter. As the basket is withdrawn into the catheter a pulling or suction effect is created, pulling an end of the thrombus or other object or material into the basket and pulling the rest of the thrombus through the vessel towards the catheter so that it too can be captured by the basket. The pulling or suction effect may be best achieved when the basket is positioned up against the object in the vessel before pulling the basket into the catheter.

The actuator may be actuatable so as to draw the basket into the catheter and so move the catheter and the basket from said first configuration to said second configuration. The medical device may be operable so as to advance the catheter over the basket and so move the catheter and the basket from said first configuration to said second configuration. The medical device may be operable so as to advance the catheter over the basket and so as to draw the basket into the catheter. Thus the basket may be withdrawn into the catheter and the catheter may be advanced over the basket at the same time. In use the movement between the catheter and the basket may cause objects in a body lumen to be drawn into the basket.

In the second configuration the first end and substantially the whole of the second end of the basket may be withdrawn into the catheter. If the thrombus is appropriately sized, the basket containing the thrombus may be withdrawn through the catheter lumen and out of the patient.

The thrombus may be broken down in the patient's lumen by a lytic agent, before being removed from the patient. The lytic agent may be delivered to the site of the thrombus through the catheter lumen, or through a lumen external to the catheter, for example though a lumen in an outer sheath.

The basket can, in the first configuration, have a first end inside the catheter and second end everted over the distal end of the catheter. In the first configuration the second end of the basket may extend radially out of the catheter and be everted over the first end of the basket and over the distal end of the catheter.

The basket may be made from wire or filamentary material. The basket may be made from braided material such as braided wire. The braiding of the basket may be tight. In other words the wires may be packed closely together, such that the spaces between the wires, if any, are small. The wires may be tightly braided so as to prevent bodily fluid such as blood from passing through the basket. For example the basket may be similar to that found in a flow diverter. The basket may have an impermeable covering to prevent fluid from passing through the basket.

The basket may be constructed so as to allow fluid to pass through the closed first end of the basket. For example the basket may comprise apertures through which fluid can pass. However, the closed first end of the basket may prevent captured objects, such as fibres from a thrombus, from passing through.

The basket may be sized so as to collect a substantially entire thrombus or other object or material. Thombi can be very large. As such the second end of the basket may be, for example from approximately 10 mm to 200 mm in length. The medical device may comprise an outer catheter, also known as an outer sheath. The outer sheath may be provided with a proximal and a distal end and a lumen therethrough. The catheter may be disposed within the lumen of the outer catheter, thereby to be configured as an inner catheter. An annular space may be provided between the inner and the outer catheters. Where an outer catheter is provided, the second end of the basket may be located in the annular space between the inner and outer catheters in the first configuration, so as to constrain the second end during delivery.

The inner and outer catheters may be moveable relative to one another so as to release the second end of the basket from between the outer catheter and the inner catheter. The second end of the basket may be free from constraint in the second configuration. The second end of the basket may be free from attachment in both the first and second configurations.

The second end may be attached to the catheter in the first configuration. Such attachment may be with ties. The ties may be releasable using a trigger wire, for example.

Where the basket is made of shape memory material, releasing the second end may allow the basket to assume its memory shape.

According to another aspect of the present invention there is provided a method of collecting objects from a body vessel, including: providing a medical device including a catheter provided with proximal end, a distal end and a lumen therethrough, and an elongate basket provided with a closed first end and an open second end; and an actuator connected to the closed first end of the basket and extending through the lumen of the catheter to the proximal end of the catheter; wherein the catheter and the basket are moveable relative to one another between a first configuration and a second configuration, wherein in the first configuration the first end of the basket is located within the distal end of the catheter and the second end of the basket extends radially out of the catheter and is everted over the first end of the basket, and in the second configuration the first end of the basket is withdrawn into the catheter and the everted second end is at least partially inverted; inserting the medical device into a body vessel; and operating the medical device so as to move the catheter and the basket from said first configuration to said second configuration thereby causing objects in a body vessel to be drawn into the basket.

The method may comprise the step of withdrawing the medical device from the body lumen, the medical device containing objects from the body vessel. In particular the basket may contain objects from the body vessel. The object containing portion of the basket may be contained within the catheter.

Where the medical device comprises an outer sheath, and where the second of the basket is held between the sheath and the inner catheter, the method may comprise the step of withdrawing the outer sheath so as to release the basket.

After operating the medical device so as to capture a thrombus or other object or material in the basket, the method may comprise advancing the outer sheath distally relative to the catheter and basket, such that the outer sheath surrounds an object containing portion of the basket, before removing the device from the patient's lumen. In this case the object containing portion of the basket may be contained within the outer sheath. Where the second end of the basket is held in the first position by ties, for example, the method may comprise the step of releasing the ties so as to release the basket.

The device described may be in the first configuration whilst tracking through the vasculature. On reaching a location proximate to the thrombus or other object, the site of interest, the device may be activated so as to move to the second configuration.

According to another aspect of the present invention there is provided a method of collecting objects from a body vessel, including: providing a medical device for collecting objects from a body vessel, the medical device including: a catheter provided with a proximal end, a distal end and a lumen therethrough; an elongate basket provided with a first end and a second end; and a wire connected to the basket and extending through the lumen of the catheter to the proximal end of the catheter; wherein the catheter and the basket are movable relative to one another between a first configuration in which the first end of the basket is located within the distal end of the catheter and the second end of the basket extends radially out of the catheter and is everted over the first end of the basket, the second end being constrained in position, and a second configuration in which the first end is withdrawn into the catheter and the second end is at least partially inverted, the second end being free from constraint; inserting the medical device into a body vessel; and operating the medical device so as to release the second end from constraint, and so as to move the catheter and the basket from said first configuration to said second configuration, such that an object in a body vessel is drawn into the basket.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
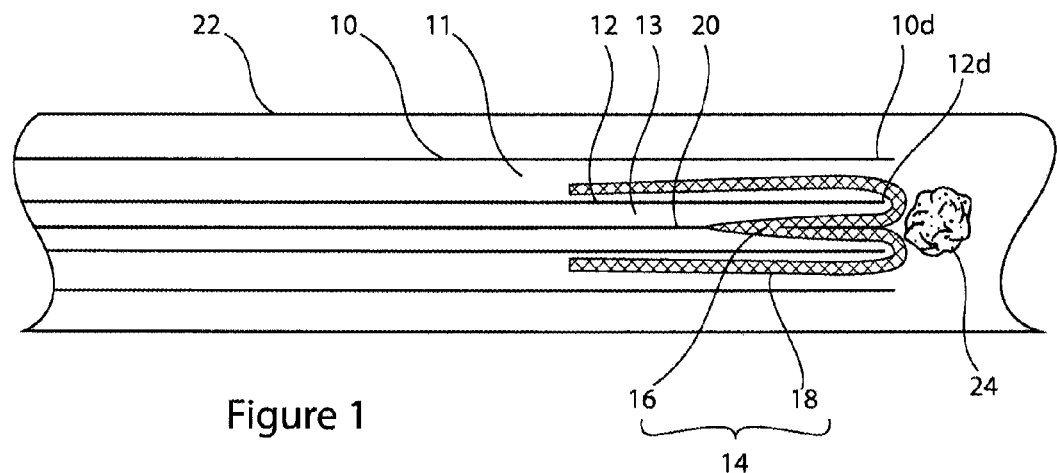
FIG. 1 shows an embodiment of a medical device for collecting objects from a body lumen, the medical device having a catheter and a basket arranged in a first configuration.

Referring to FIG. 1, there is shown in schematic form an embodiment of a medical device for collecting objects from a body lumen 22. The medical device is shown inside a patient's vessel 22; within which there is also a thrombus 24. The medical device comprises an outer catheter 10 disposed concentrically around an inner catheter 12, and an object collecting member 14, hereafter called a basket 14.

The inner 12 and outer 10 catheters are in the form of elongate tubes having proximal (not shown) and distal 10d, 12d ends. In use the distal ends 10d, 12d of the catheters are positioned proximate the thrombus or object or material to be removed and the proximal ends are outside of the patient. The outer catheter 10 comprises a lumen in which the inner catheter 12 is disposed. The catheters are arranged such that an annular gap 11 is provided between the inner 12 and outer 10 catheters. The inner catheter 12 also comprises a lumen 13, into which the basket 14 may be withdrawn.

The basket comprises a first end portion 16 and a second end portion 18. The first end portion 16 of the basket 14 is connected to an actuator wire 20. The wire 20 is disposed inside the lumen 13 of the inner catheter 12 and extends through the lumen 13 to an actuating portion of the medical device which in use is external to the patient's body. The first end portion 16 of the basket 14 is, in a first configuration, housed within the lumen 13 of the inner catheter 12. The basket 14 extends, from the first end portion 16, out of the end of the inner catheter 12 and is everted so as to extend backwardly over itself around the inner catheter and inside the outer catheter 10 such that the second end portion 18 of the basket 14 is housed in the annular gap 11 between the inner catheter 12 and the outer catheter 10.

In this case the distal ends of the catheters 10, 12 are aligned with one another and are positioned such that the basket 14 abuts the thrombus 24. The basket 14 surrounds part of the thrombus 24 when it is moved up against the thrombus 24, giving it a grip on the thrombus 24 and thus aiding withdrawal/pulling of the thrombus 24 into the basket 14 when the device is used.

The basket 14 comprises a braided wire basket made of shape memory material, or of spring steel, for example. Such a basket 14 may be flexible so as to fit around thrombi 24 of various shapes and sizes, and so as to be able to be withdrawn into the narrow lumen 13 of the inner catheter 12. The braiding of the basket 14 is tight, such that the spaces between the wires, if any, are small. It is not necessary for the basket 14 to allow blood or other fluid to pass through it. The thrombus removal process may be carried out very quickly and as such preventing blood flow through the vessel 22 whilst the procedure is carried out does not harm the patient.

Figure 2:
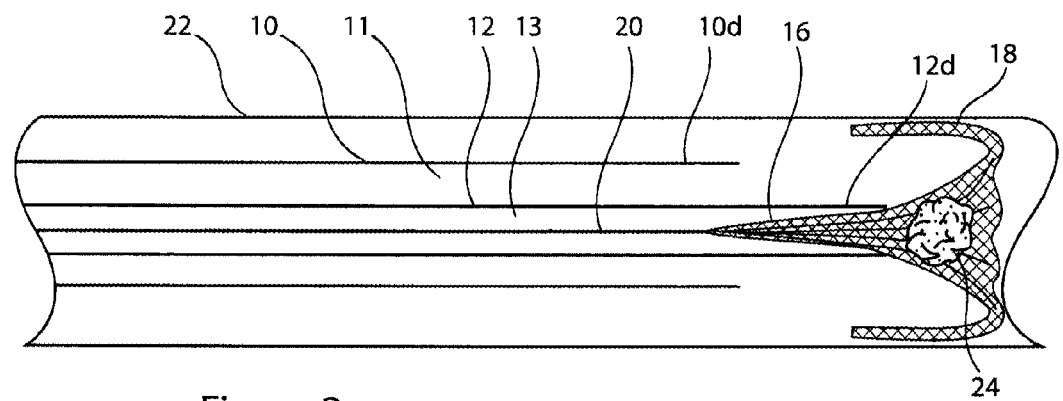
FIG. 2 shows the medical device of FIG. 1 after the outer sheath has been withdrawn from around the basket.

FIG. 2 shows the medical device of FIG. 1 after the outer catheter 10 has been withdrawn relative to the inner catheter 12. The outer catheter 10 is provided so as to cover the basket 14 and prevent it from springing open during introduction of the device. Once the outer catheter 10 has been withdrawn the second end portion 18 of the basket 14 is no longer constricted and is able to spring open outwardly. The basket 14 opens until it comes into contact with the internal walls of the vessel 22, scraping along the sides of the lumen so as to surround the thrombus 24. The second end portion 18 of the basket 14 remains everted, backwards over itself, and contacts the sides of the vessel 22.

Figure 3:
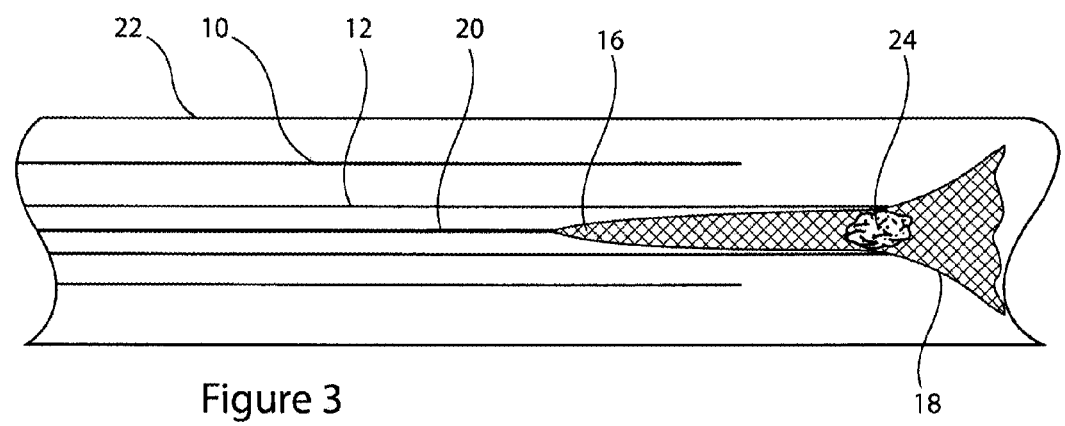
FIG. 3 shows the medical device of FIGS. 1 and 2, the catheter and the basket arranged in the second configuration.

FIG. 3 shows the medical device of FIGS. 1 and 2 in a second configuration, in which the first end portion 16 of the basket 14 and part of the second end portion 18 are withdrawn into the inner catheter 12 such that the basket 14, and the thrombus 24 inside it, is substantially contained within the inner lumen 12. The basket 14 can be from 10 to 200 mm long, depending on the length and size of the material/thrombus 24 to be captured. The basket 14 is designed to be long enough to trap the entirety of the thrombus 24. In particular, the everted second portion 18 of the basket 14 is designed to be long enough to trap the entirety of the thrombus 24. In one mode movement of the basket 14, from the first configuration shown in FIG. 1 to the second configuration shown in FIG. 3, is actuated by pulling on the actuating element 20. By pulling back on the actuating element 20 the second end portion 18, the open end of the basket 14, is pulled into the distal end 12d of the inner catheter 12. This action causes the second end portion 18 of the basket 14 to roll inwardly, thus drawing, as if pulling or sucking, the thrombus 24 into the closing basket. The thrombus 24 is thus trapped bit-by-bit in the basket 14 and withdrawn into the inner catheter 12. As a result of the relative movement between the inner catheter 12 and the basket 14 from the first configuration to the second configuration the thrombus 24 is thus drawn into the inner catheter 12, inside the basket 14.

Where the thrombus 24 is small enough to be withdrawn through the lumen of the inner catheter 12 continued retraction of the actuating element 20 allows withdrawal of the basket 14, in which the thrombus 24 is held, through the lumen 13 of the inner catheter 12. The basket 14 containing the thrombus 24 may thus be completely removed from the patient's vessel 22 through the lumen 13 of the inner catheter 12. As such this embodiment provides a single tool which is used in a single stage to remove the thrombus from a patient's vessel.

Where the thrombus 24 is too large to be pulled into the lumen 13 of the inner catheter 12, the outer catheter 10 or sheath may be advanced over the thrombus 24. In this manner the thrombus 24 can be held within the basket 14 and also within the outer catheter 10 so that it can then be removed from the patient.

In some instances, instead of pulling back on the actuator wire 20, the inner catheter 12 may be advanced over the basket 14. This movement from the first configuration to the second configuration will have the same effect of withdrawing the basket 14 into the inner catheter 12.

The apparatus may be operated by advancing the inner catheter 12 over the basket 14 as the actuator wire 20 is withdrawn into the inner catheter 12. A combination of the two movements may be performed together so that as the basket 14 is withdrawn in the inner catheter 12 the inner catheter 12 is also advanced over the basket 14.

Figure 4:
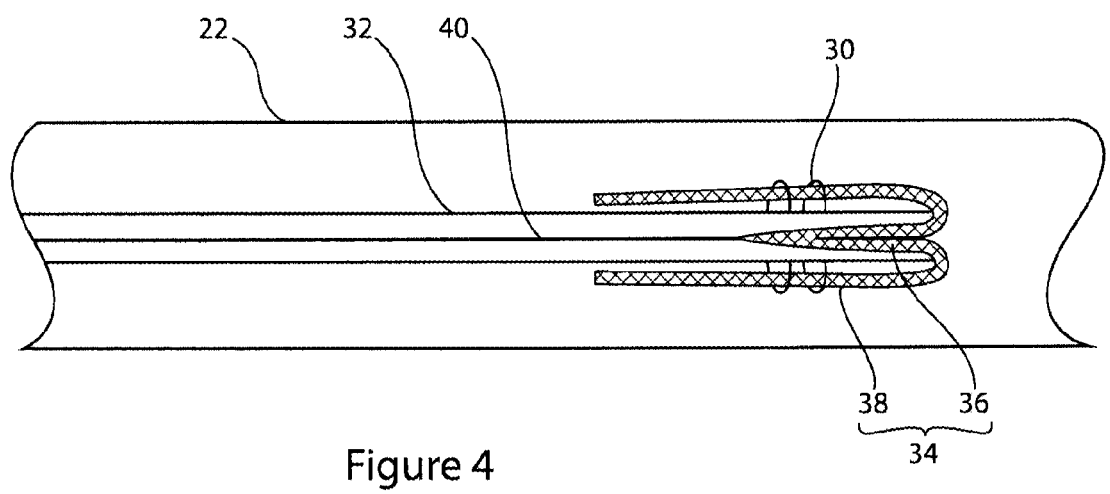
FIG. 4 shows another embodiment of a medical device for collecting objects from a body lumen.

FIG. 4 shows another embodiment of a medical device for collecting objects from a body vessel 22. The medical device comprises an inner catheter 32, and a basket 34 having first 36 and second 38 end portions.

In this device ties 30 are provided to secure the second end portion 38 of the basket 34 in its everted position around the outside of the inner catheter 32. In this embodiment the outer catheter is not required to secure the basket 34 in its first configuration. Trigger wires (not shown) may be used to release the ties 30 so as to enable the basket 34 to open outwardly as a result of its shape memory characteristics, and to be withdrawn into the inner catheter 32. An outer catheter (not shown) may be provided for use in delivery of the medical device to a location adjacent a thrombus inside a vessel.

It is to be understood that the different features of the various embodiments described herein can be combined together.

The disclosures in GB application number 1200333, from which this application claims priority, and in the abstract accompanying this application, are incorporated herein by reference.

The invention claimed is:

1. A medical device for collecting objects from a body vessel, including:
   a catheter provided with a proximal end, a distal end and a lumen therethrough;
   an elongate basket provided with a closed first end and an open second end; and
   an actuator connected to the closed first end of the basket and extending through the lumen of the catheter to the proximal end of the catheter;
   wherein the catheter and the basket are movable relative to one another between a first configuration in which the first end of the basket is located within the distal end of the catheter and the second end of the basket extends radially out of the catheter and is everted over at least part of the first end of the basket, and a second configuration in which the first end is withdrawn into the catheter and the everted second end is at least partially inverted; and
   wherein, the medical device is operable so as to move the catheter and the basket from said first configuration to said second configuration, said movement in use causing objects in a body vessel to be drawn into the basket.

2. A medical device according to claim 1, wherein the basket is made of shape memory material.

3. A medical device according to claim 1, wherein the basket is made of wire or filamentary material.

4. A medical device according to claim 3, wherein the wire or filamentary material is braided.

5. A medical device according to claim 4, wherein the wire or filamentary material is tightly braided so as to prevent fluid from passing through the basket.

6. A medical device according to claim 1, wherein the basket has an impermeable covering.

7. A medical device according to claim 1, wherein the actuator is a wire.

8. A medical device according to claim 1, wherein the basket comprises apertures sized to allow fluid to pass through the closed first end of the basket but prevent the captured objects from passing therethrough.

9. A medical device according to claim 1, wherein the actuator is actuatable so as to draw the basket into the catheter and so move the catheter and the basket from said first configuration to said second configuration.

10. A medical device according to claim 1, wherein, the medical device is operable so as to advance the catheter over the basket and so move the catheter and the basket from said first configuration to said second configuration.

11. A medical device according to claim 1, wherein in the second configuration the first end and substantially the whole of the second end of the basket may be withdrawn into the catheter.

12. A medical device according to claim 1, wherein the basket is from 10 to 200 mm in length.

13. A medical device according to claim 1, wherein the second end is constrained in the first position and free from constraint in the second position.

14. A medical device according to claim 1 including an outer sheath provided with a proximal and a distal end and a lumen therethrough, wherein the catheter is disposed within the lumen of the outer sheath, thereby to be configured as an inner catheter, an annular space being provided between the inner catheter and the outer sheath, and wherein in said first configuration the second end of the basket is located in the annular space between the inner catheter and outer sheath.

15. A medical device according to claim 14 wherein the second end of the basket is free from attachment and wherein the inner catheter and outer sheath are moveable relative to one another so as to release the second end of the basket from between the outer sheath and the inner catheter.

16. A medical device for collecting objects from a body vessel, including:
   a catheter provided with a proximal end, a distal end and a lumen therethrough;
   an elongate basket provided with a first end and a second end; and
   an actuator connected to the first end of the basket and extending through the lumen of the catheter to the proximal end of the catheter;
   wherein the catheter and the basket are movable relative to one another between a first configuration in which the first end of the basket is located within the distal end of the catheter and the second end of the basket extends radially out of the catheter and is everted over the first end of the basket, the second end being constrained in position, and a second configuration in which the first end is withdrawn into the catheter and the everted second end is at least partially inverted, the second end being free from constraint; and
   wherein, the medical device is operable so as to release the second end from constraint, and move the catheter and the basket from said first configuration to said second configuration, said movement in use causing objects in a body vessel to be drawn into the basket.

17. A medical device according to claim 16, wherein the first end of the basket is closed and the second end open.

18. A medical device according to claim 16, wherein the basket is made of shape memory material, said material having a memory shape, and wherein releasing the second end portion allows the basket to assume its memory shape.

19. A method of collecting objects from a body vessel, including:
providing a medical device including a catheter provided with proximal end, a distal end and a lumen therethrough, and an elongate basket provided with a closed first end and an open second end; and an actuator connected to the closed first end of the basket and extending through the lumen of the catheter to the proximal end of the catheter; wherein the catheter and the basket are moveable relative to one another between a first configuration and a second configuration, wherein in the first configuration the first end of the basket is located within the distal end of the catheter and the second end of the basket extends radially out of the catheter and is everted over the first end of the basket, and in the second configuration the first end and at least part of the second end of the basket is withdrawn into the catheter and the everted second end is at least partially inverted;
inserting the medical device into a body vessel; and
operating the medical device so as to move the catheter and the basket from said first configuration to said second configuration thereby causing objects in a body vessel to be drawn into the basket.

20. The method of claim 19, wherein the medical device further comprises an outer sheath having a lumen, the catheter is disposed within the lumen of the outer sheath in the first configuration, and the second end of the basket is disposed within an annular space defined between the outer sheath and the catheter in the first configuration, and the outer sheath is moveable relative to the catheter and the basket to expose the second end of the basket.

* * * * *